United States Patent [19]
Perego et al.

[11] Patent Number: 6,015,906
[45] Date of Patent: *Jan. 18, 2000

[54] DIMETHYLAMINE BENZOATE OR P-ANISATE CATALYSED PROCESS FOR THE PREPARATION OF 4-(NITROPHENYL)-DIHYDROPYRIDINES

[75] Inventors: Bruno Perego; Elso Manghisi, both of Lomagna, Italy

[73] Assignee: Lusochimica S.p.A., Lomagna, Italy

[ * ] Notice: This patent issued on a continued prosecution application filed under 37 CFR 1.53(d), and is subject to the twenty year patent term provisions of 35 U.S.C. 154(a)(2).

[21] Appl. No.: 08/894,389
[22] PCT Filed: Mar. 14, 1996
[86] PCT No.: PCT/EP96/01090
　§ 371 Date: Aug. 18, 1997
　§ 102(e) Date: Aug. 18, 1997
[87] PCT Pub. No.: WO96/29310
　PCT Pub. Date: Sep. 26, 1996

[30] Foreign Application Priority Data

Mar. 20, 1995 [IT] Italy .................. MI95A0540

[51] Int. Cl.$^7$ .................................. C07D 211/86
[52] U.S. Cl. .................................. 546/321
[58] Field of Search ............................. 546/321

[56] References Cited

PUBLICATIONS

CA 114:122068, Serra et al., 1991.

CA 116:59220, Serra et al., 1992.

European.Pharmacopoeia Supplement 1998 pp. 396–397.

*Primary Examiner*—Jane Fan
*Attorney, Agent, or Firm*—Walter H. Schneider

[57] ABSTRACT

A method for the preparation of 4-(nitrophenyl)-dihydropyridines by reacting a benzaldehyde with an acetoacetate and reacting the resulting benzylidene derivative with an enamine derivative. Both reactions are catalyzed by dimethylamine benzoate or p-anisate.

2 Claims, No Drawings

DIMETHYLAMINE BENZOATE OR P-ANISATE CATALYSED PROCESS FOR THE PREPARATION OF 4-(NITROPHENYL)-DIHYDROPYRIDINES

This is a 371 of PCT/EP96/01090 filed Mar. 14, 1996 now WO 96/29310.

The present invention relates to a process for the preparation of 4-(nitrophenyl)dihydropyridines.

These products are widely used due to their remarkable pharmaceutical properties, and up to now they were prepared according to different synthetic methods. For example, Hantzsch's synthesis (Ann. 215, 1, 72; 1882) is made use of to prepare in a single step the 3,5-dicarboxylic acid symmetric esters, using a mole of aldehyde, 2 moles of acetoacetic ester and ammonia.

On the other hand, for the preparation of the asymmetric esters, Knoevenagel synthesis is employed, (Ber. 31, 370; 1898) first reacting an aldehyde with an acetoacetate in the presence of piperidine, subsequently treating the resulting benzylidene derivative with the suitable aminocrotonate.

Knoevanagel condensation is exhaustively described by G. Jones in Organic Reactions, 15, 1967, p. 204–599.

A number of methods and patents concerning the preparation of dihydropyridines exist in literature.

Among these, EP 0,124,743 and EP 0,173,126 disclose the preparation of the benzylidene derivatives with suitable catalysts, such as piperidine acetate in the first Patent and, inter alia, o-anisidine and m-toluidine in the second Patent. On the other hand, EP 319,814 discloses the final closure reaction of one of these important dihydropyridines, catalyzed by diisopropylamine acetate or dimethylbenzylamine acetate.

Now it has surprisingly been found that dihydropyridine asymmetric esters can be prepared in high yield and purity, with remarkable savings in time and energy, and therefore with a low cost, using as reaction catalysts organic salts that up to now have never been considered.

The dihydropyridines of the invention have the general formula (I)

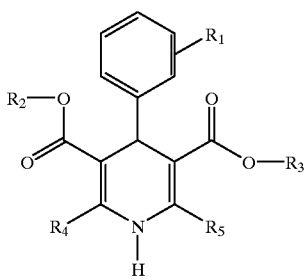

(I)

wherein $R_1$ is a nitro group at the 2 or 3 position; $R_2$ and $R_3$, which are different from each other, are a methyl, ethyl, isopropyl, 2-methoxyethyl or isobutyl group, whereas $R_4$ and $R_5$ are methyl groups.

Compounds (I) are prepared, according to the invention, from a benzylidene derivative of general formula (II)

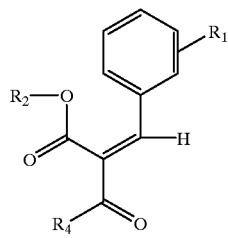

(II)

wherein $R_1$, $R_2$ and $R_4$ have the meanings defined above, by reaction with an enamine derivative of general formula (III)

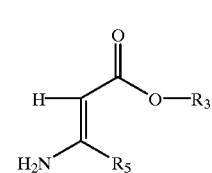

(III)

wherein $R_3$ and $R_5$ have the meanings defined above.

The benzylidene derivative (II) is in turn prepared by reacting a benzaldehyde of general formula (IV)

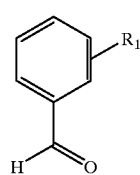

(IV)

wherein $R_1$ has the meanings defined above, with an acetoacetic ester of general formula (V)

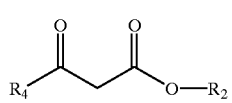

(V)

wherein $R_2$ and $R_4$ have the meanings defined above.

Both the above reactions can be carried out in a lower $C_{1-4}$ alcohol and are catalyzed by dimethylamine benzoate or p-anisate.

The use of the catalyst according to the invention makes it surprisingly possible to carry out the reaction necessary for the preparation of (II) in mild conditions (reaction temperature ranging from 20° to 40° C.). In this way, the formation of undesired side-products is restricted and a highly pure intermediate (II) is obtained in a high yield, with remarkable energetic savings and therefore at lower costs.

The use of dimethylamine benzoate or anisate in the subsequent reaction, moreover, makes it possible for (I) to form already after a few hours heating, also affording in this case the advantage of energetic savings and consequent low costs.

On the contrary, when the reaction for the preparation of the main product (I) is carried out with no use of catalysts, heating under reflux up to 24 hours is necessary (as disclosed, for example, in EP 124,743).

Moreover, the use of dimethylamine anisate or benzoate minimizes the formation of the main undesired impurities of these dihydropyridines, i.e. the corresponding dicarboxylic symmetric esters of general formula (II) wherein $R_2$ and $R_3$ are the same.

In the process of the invention, the catalyst moles range from 0.01 to 0.06 per mole of nitrobenzaldehyde and from 0.005 to 0.015 per mole of nitrobenzylidene derivative.

From the comparison between the data deducible from the Registry of Toxic Effects of Chemical Substance, moreover, the catalysts of the invention turn out to be less toxic than those used up to now in the above cited patents.

For example, in EP 0,124,743 piperidine is used as the catalyst. Said product involves evident handling problems due to its characteristics of toxicity.

Finally, the use of a single, scarcely toxic catalyst makes the search for any traces thereof in the final product (I) easier.

The following examples further illustrate the process of the invention without limiting it.

EXAMPLE 1 a) 300 kg of ethyl acetoacetate and 348 kg of 3-nitrobenzaldehyde are suspended in 1550 l of isopropanol. After that 5.235 kg of p-anisic acid and 4.4 kg of 33% dimethylamine in ethanol are added. The mixture is warmed for about 30' at about 35° C. to obtain a solution. The reaction mixture is left to cool at 20/25° C. and then it is cooled for about 12 hours with running water and for a further 24 hours at about 0° C. with brine, then is centrifuged, washing with isopropanol.

After drying, 578 kg of ethyl 2-(3-nitrobenzylidene) acetoacetate are obtained, in an about 95% yield.

b) 362 kg of ethyl 2-(3-nitrobenzylidene)acetoacetate and 158.3 kg of methyl 3-aminocrotonate are suspended in 840 l of isopropanol and treated with 2.2 kg of p-anisic acid and 1.85 kg of 33% dimethylamine in ethanol. Upon heating, a solution is obtained which is refluxed for about 12 hours, after that it is cooled with water and then with brine at about −5° C. and the resulting precipitate is centryfuged.

By recrystallization from isopropanol, 476 kg of Nitrendipine are obtained in an about 96% yield.

The content in dimethyl and diethyl esters, by HPLC analysis, turns out to be lower than 0.1% for each of said impurities.

EXAMPLE 2 a) 200 kg of 2-methoxyethyl acetoacetate and 185.1 kg of 3-nitrobenzaldehyde are suspended in 800 l of isopropanol. Then 5.65 kg of p-anisic acid and 5.05 kg of 33% dimethylamine in ethanol are added, heating for about 30' at about 35° C. to obtain a solution. The reaction mixture is left to cool at 20/25° C. and then it is cooled for about 12 hours with running water and for a further 24 hours at about 0° C. with brine, then is centrifuged, washing with isopropanol.

After drying, 327 kg of 2-methoxyethyl 2-(3-nitrobenzylidene) acetoacetate are obtained, in an about 91% yield.

b) 490 kg of 2-methoxyethyl 2-(3-nitrobenzylidene) acetoacetate and 244.4 kg of isopropyl 3-aminocrotonate are suspended in 1500 l of isopropanol and treated with 3 kg of p-anisic acid and 2.5 kg of 33% dimethylamine in ethanol. Upon heating, a solution is obtained which is refluxed for about 10 hours, after that it is cooled with water and then with brine at about 0° C. and the resulting precipitate is centrifuged.

By recrystallization from isopropanol, 657 kg of Nimodipine are obtained in an about 94% yield.

The content in 2-methoxyethyl and diisopropyl esters, by HPLC analysis, turns out to be lower than 0.1% for each of said impurities.

We claim:

1. A process for the preparation of asymmetric esters of 4-(nitrophenyl)dihydropyridines of general formula (I)

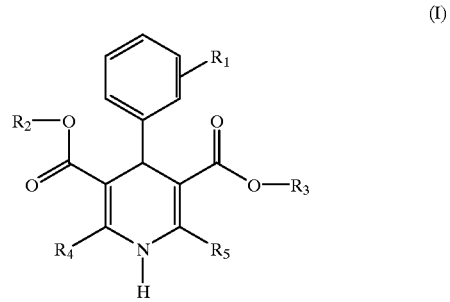

(I)

wherein $R_1$ is a nitro group at the 2 or 3 position; $R_2$ and $R_3$, which are different from each other, are a methyl, ethyl, isopropyl, 2-methoxyethyl or isobutyl group; $R_4$ and $R_5$ are methyl groups,
by reacting a benzylidene derivative of general formula (II)

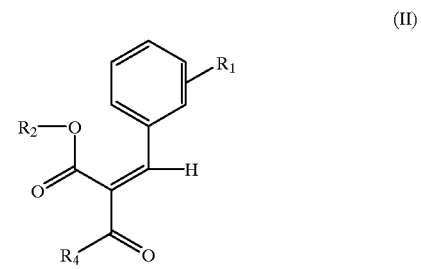

(II)

wherein $R_1$, $R_2$ and $R_4$ have the meanings defined above, with an enamine derivative of general formula (III)

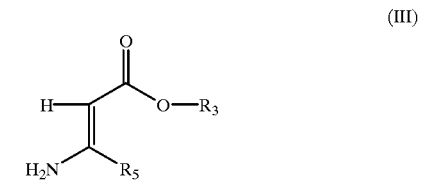

(III)

wherein $R_3$ and $R_5$ have the meanings defined above, chacterized in that said reaction is carried out in the presence of dimethylamine benzoate or p-anisate as the catalyst, said catalyst being present in an amount of 0.005–0.015 mole per mole of benzylidene derivative.

2. A process for the preparation of asymmetric esters of 4-(nitrophenyl)dihydropyridine of the general formula (I)

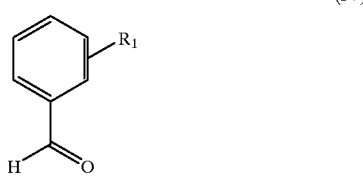

(IV)

wherein $R_1$ is a nitro group at the 2 or 3 position; $R_2$ and $R_3$, which are different from each other, are a methyl, ethyl, isopropyl, 2-methoxyethyl or isobutyl group; $R_4$ and $R_5$ are methyl groups;

which comprises reacting at a temperature of 20–40° C. a benzaldehyde of the general formula (IV)

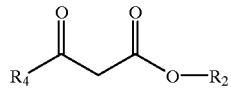
(V)

wherein $R_1$ has the meaning defined above;

with an acetoacetic ester of the general formula (V)

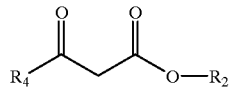
(V)

wherein $R_2$ and $R_4$ have the meainings defined above;

and reacting the resultant benzylidene derivative of the general formula (II)

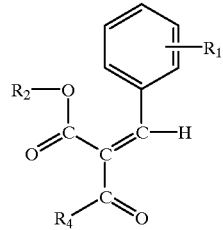
(II)

wherein $R_1$, $R_2$ and $R_4$ have the meanings defined above; with an enamine derivative of the general formula (III)

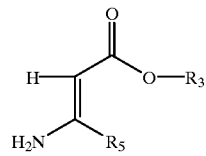
(III)

wherein $R_3$ and $R_5$ have the meanings defined above; both reactions being carried out in a solvent comprising a lower aliphatic $C_{1-4}$ solvent and in the presence of a catalyst selected from dimethylamine benozoate or p-anisate, the amount of catalyst being 0.01–0.06 mole per mole of nitrobenzaldehyde and 0.005–0.015 mole per mole of nitrobenzylidene derivative; and recovering the resultant ester of 4-(nitrophenyl)dihydropyridine.

* * * * *